United States Patent [19]

Turner et al.

[11] Patent Number: 5,716,878
[45] Date of Patent: Feb. 10, 1998

[54] RETRACTABLE PROBE SYSTEM WITH IN SITU FABRICATION ENVIRONMENT PROCESS PARAMETER SENSING

[75] Inventors: Terry R. Turner, Austin; James F. Belcher, Plano; Gary W. Andrews, Dallas, all of Tex.

[73] Assignee: Texas Instruments Incorporated, Dallas, Tex.

[21] Appl. No.: 787,559

[22] Filed: Jan. 22, 1997

Related U.S. Application Data

[62] Division of Ser. No. 252,817, Jun. 2, 1994.

[51] Int. Cl.⁶ .......................... G01N 27/00; H01L 21/00
[52] U.S. Cl. ............... 438/17; 204/298.03; 204/298.32; 216/61; 156/345; 324/754
[58] Field of Search ..................... 156/627.1, 345; 216/61; 204/298.03, 298.32

[56] References Cited

U.S. PATENT DOCUMENTS

| | | | |
|---|---|---|---|
| 4,316,791 | 2/1982 | Taillet | 204/298 |
| 4,458,202 | 7/1984 | Nefedov et al. | 324/204 |
| 4,668,366 | 5/1987 | Zarowin | 204/192.1 |
| 5,082,517 | 1/1992 | Moslehi | 156/345 |
| 5,159,267 | 10/1992 | Anderson | 324/158 R |
| 5,167,748 | 12/1992 | Hall | 156/345 |
| 5,169,407 | 12/1992 | Mase et al. | 29/25.01 |
| 5,339,039 | 8/1994 | Carlile et al. | 324/655 |
| 5,433,813 | 7/1995 | Kuwabara | 156/345 |

*Primary Examiner*—R. Bruce Breneman
*Assistant Examiner*—Michael E. Adjodha
*Attorney, Agent, or Firm*—W. James Brady, III; Richard L. Donaldson

[57] ABSTRACT

A retractable probe system (12) senses in situ a plurality of predetermined process parameters of a wafer (24) fabrication environment (16) and includes a sensing device (47) for sensing the predetermined process parameters, a probe arm (46) for holding sensing device (47) and having sufficient length to extend sensing device (47) into a predetermined location of the fabrication environment (16). A housing (36) receives the sensing device (47) and probe arm (46). A locator mechanism (52, 42, and 44) controllably locates sensing device 47) and probe arm (46) within fabrication environment (16) and within housing (36). An isolator mechanism (34) isolates sensing device (47) and probe arm (46) within housing (36) and essentially out of gases communication with fabrication environment (16). Cleaning mechanism (54) cleanses sensing device (47) within housing (36) and permits sensing device (47) to be immediately thereafter located in fabrication environment (16).

10 Claims, 3 Drawing Sheets

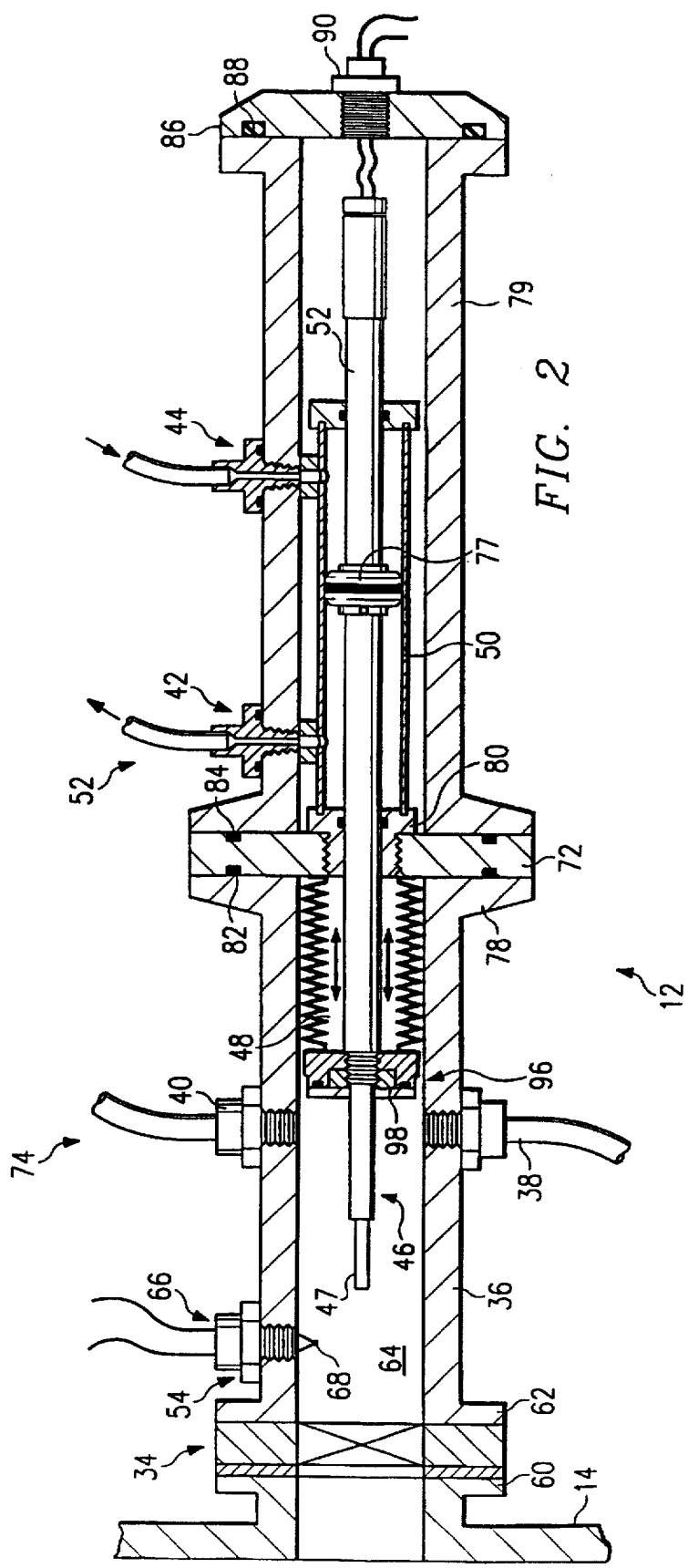
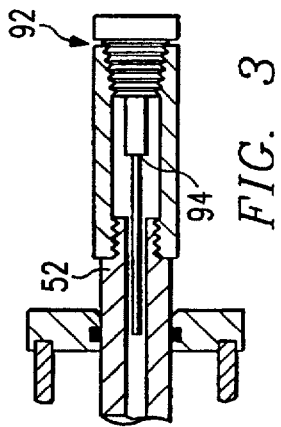

RETRACTABLE PROBE SYSTEM WITH IN SITU FABRICATION ENVIRONMENT PROCESS PARAMETER SENSING

This is a division of application Ser. No. 08/252,817, filed Jun. 2, 1994.

TECHNICAL FIELD OF THE INVENTION

The present invention generally relates to semiconductor wafer processing and, more particularly, to a retractable probe system that provides in situ sensing of fabrication reactor process parameters together with a method and system for cleansing the sensor.

BACKGROUND OF THE INVENTION

Semiconductor wafer manufacturers generally use a fabrication reactor having a process chamber in which to develop a fabrication environment for depositing various films on one or more semiconductor wafers. Processes that semiconductor device manufacturers use establish fabrication environments that form, for example, epitaxial semiconductor layers, dielectrics (e.g., silicon nitride, silicon oxide, or oxinitrides), metals (e.g., tungsten), polycrystalline silicon, and doped oxides. There is the need to monitor process parameters such as electron temperature, density, and sheath potential in the fabrication environment of the process chamber and during the fabrication process, i.e., in situ.

Known techniques for measuring fabrication environment process parameters use an electrostatic sensor built on a probe called an electrostatic probe. Use of electrostatic probes in situ presents numerous problems, including the problem of depositing films on the electrostatic probe. In plasma processing, including both etch or deposition processes, there is a continuing deposition of material films such as organic compounds, polymers, $SiO_2$, and $Si_3N_4$. These films can significantly change the electrostatic probe sensing surface characteristics. For example, in one well-known electrostatic probe, the single Langmuir probe, deposited films may induce measurement errors of more than 200%.

Because these films change probe characteristics and limit the probe's ability to make repeatable measurements, use of electrostatic probes such as the Langmuir probe requires the periodic removal of these films. The cleaning process has generally been performed in one of three ways, all of which have serious drawbacks. One known method to clean an electrostatic probe is to open the fabrication reactor and remove the probe for cleaning. This process further entails either etching or physically scraping off the films to expose a fresh clean probe sensing surface. The drawback of this technique is, of course, excessive fabrication reactor downtime and the changes in probe surface area that occur during the abrasive material removal steps.

Another technique for probe cleaning applies a very high bias voltage to the electrostatic probe and relies on either electron or ion bombardment to remove the unwanted films. A problem of this technique is that it generates excessively high temperatures at the probe sensing tip. These temperatures may result in thermal or secondary emissions of tip material into the reactor chamber or onto the surface of semiconductor wafers.

Yet another approach to overcome the problem of film deposition on the electrostatic probe removes the probe from the bulk of the plasma in the fabrication environment during parameter sensing. This technique senses process parameters in the sheath region of the reactor chamber walls. This approach attempts to use the sheath voltage to retard film deposition on the probe. This approach does not work, however, because electrically neutral particles, which the sheath potential does not affect, still deposit films on the probe.

SUMMARY OF THE INVENTION

There is a need, therefore, for an improved method and apparatus for in situ monitoring of electron temperature, electron density, sheath potential, and other fabrication environment process parameters.

There is a need for a method and apparatus for sensing semiconductor fabrication environment process parameters that avoids the detrimental effects from depositing films on the sensing device.

There is a further need for an improved method and system for sensing semiconductor wafer fabrication environment process parameters that avoids the downtime problem and probe surface area changes from which existing methods and systems suffer.

There is a need for an improved method for sensing semiconductor wafer fabrication reactor process parameters that avoids the thermal stresses and secondary tip material emissions that associate with existing methods of sensing fabrication reactor process parameters.

There is yet the need for an improved semiconductor wafer fabrication reactor process parameter sensing method and system that avoids the disadvantageous effects of depositing not only charged particles, but also neutrals that can affect parameter sensing accuracies.

The method and system of the present invention, therefore, overcome the above-stated problems to satisfy the above-stated needs and provide an improved retractable probe system with in situ fabrication environment process parameter sensing. The present invention provides a retractable probe for in situ semiconductor device fabrication environment operation that substantially eliminates or reduces disadvantages and limitations associated with prior methods and devices for sensing semiconductor wafer fabrication environment process parameters.

The retractable probe of the present invention senses predetermined process parameters of the semiconductor device fabrication environment in situ. A probe arm holds the sensing device and has sufficient length to extend the sensing device to a predetermined location in the semiconductor wafer fabrication environment. A housing receives the sensing device and the probe arm. A locator mechanism controllably positions the sensing device and the probe arm within the fabrication environment for parameter sensing and within the housing to remove the sensing device from the fabrication environment. An isolation mechanism isolates the sensing device and probe arm when they are within the housing so that they are out of gaseous communication with the fabrication environment. The invention further includes a cleansing mechanism for cleansing the sensing device within the housing. After sensing device cleansing, the probe arm and sensing device may reenter the fabrication environment for in situ process parameter sensing.

In the present embodiment, the sensing device is cleansed while out of gaseous communication with the fabrication environment. The housing includes an evacuation mechanism for evacuating gases and free radicals that exist in the housing from the fabrication environment. The cleansing mechanism includes a biasing mechanism for biasing the sensing device to remove materials deposited from the fabrication environment. In addition, a control mechanism may be associated with the retractable probe to automatically control the operation of the locator mechanism, the isolator mechanism, and the cleansing mechanism. The sensing device may be, for example, a temperature sensor for sensing the temperature of the semiconductor device fabrication environment, an electron density sensor for determining the fabrication environment electron density, or a sheath potential sensor for sensing the potential of a plasma sheath during plasma processing. All of these types of sensing devices may, for example, be an electrostatic sensing device.

A technical advantage of the present invention is that it is simple to implement for in situ movement of the processing probe during wafer processing. The probe arm and sensor may be inserted into and removed from the semiconductor device fabrication environment easily to permit sensing device cleansing.

Another technical advantage of the present invention is that it permits full scale production of semiconductor wafers without having to break the vacuum that often exists in the process chamber, remove the probe, scrape off or otherwise abrasively clean the sensor and then restore process chamber vacuum for further wafer processing and parameter sensing. Avoiding these steps permits continuous operation of the fabrication reactor and, consequently, continuous processing of semiconductor wafers.

Another technical advantage of the present invention is that it improves the sensing accuracy of the sensing device. By removing the sensing device from the fabrication environment for immediate cleansing, the process of the present invention removes the small amounts of deposited material that, over time, adversely affect process parameter measurements. With the present invention, there is no need to later scrape or abrasively clean the sensing device surface. The present invention further eliminates the need to clean the sensing device by ion bombardment or thermally. This avoids the detrimental effects of changing the probe surface area and changes in sensing accuracy that deposited films may produce. As a result, not only does the method and system of the present invention permit full scale continuous wafer production, but also the present method and system improves the sensing accuracy of whatever sensing device the present probe system may use. By improving the sensing accuracy, the quality of the resulting semiconductor device can directly improve.

BRIEF DESCRIPTION OF THE DRAWINGS

The invention and its modes of use and further advantages are best understood by reference to the following description of illustrative embodiments when read in conjunction with accompanying drawings, wherein:

FIG. 2 provides a more detailed side schematic view of the present embodiment that FIG. 1 illustrates;

FIG. 3 shows one embodiment of an electrical connector the present embodiment may use.

DETAILED DESCRIPTION OF THE INVENTION

For a more complete understanding of the invention and for further advantages thereof, reference is now made to the following detailed description, which is to be taken in conjunction with the accompanying FIGURES.

Figure 1:
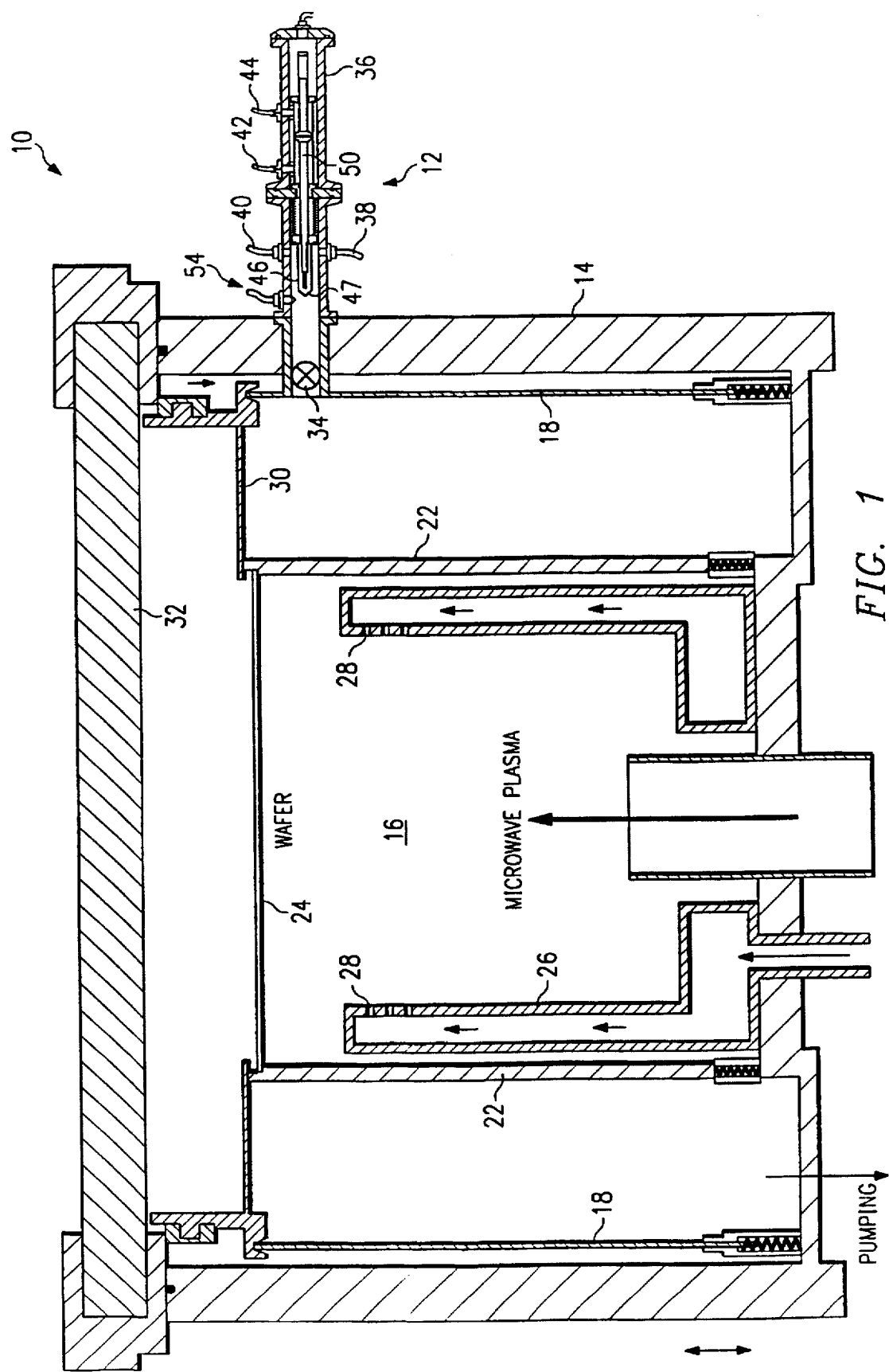
FIG. 1 provides a side schematic diagram of a single-wafer rapid thermal/plasma multi-processing reactor that incorporates the present embodiment of the invention.

FIG. 1 provides a side schematic diagram of a fabrication reactor process chamber 10 with which retractable probe system 12 may operate. Process chamber 10 may be, for example, within a fabrication reactor of a single-wafer rapid thermal/plasma multi-processing fabrication system. In the example of FIG. 1, process chamber 10 includes process chamber wall 14 that surrounds fabrication environment 16. Process chamber liner 18 provides an outside boundary for fabrication environment 16. Support pins 22 support semiconductor wafer 24. Inside the boundary that support pins 22 define and within process chamber liner 18 is, for example, plasma gas injection module 26. Plasma gas injection module 26 forms a sheath that directs plasma into fabrication environment 16 via injection holes 28 to produce semiconductor device plasma fabrication environment 16. Retaining device 30 may be included for retaining the position of pins 22 relative to semiconductor wafer 24. In addition, quartz window 32 provides a path for radiant heat to flow and elevate the semiconductor wafer 24 temperature, such as during heat reactive fabrication processes.

It is the process parameters such as process temperature, electron density, and the potential of the plasma gas injection module 26 within fabrication environment 16 that retractable probe system 12 of the present embodiment senses. Retractable probe system 12 includes an isolation mechanism in the form of valve 34 that isolates housing 36. Housing 36 includes ports 38 and 40 that, respectively, flow cleansing gases into and various gases and free radicals from housing 36. These gases and free radicals may come from fabrication environment 16. Furthermore, ports 42 and 44 control the flow of a control medium, such as a gas or hydraulic liquid, to control the position of probe arm 46, which includes sensing device 47, within actuator 50. Sensing device 47 senses process parameters of fabrication environment 16. Retractable probe system 12 extends probe arm 46 through process chamber wall 14 and process chamber liner 18, past wafer pins 22 and into fabrication environment 16. Within housing 36 is also cleansing mechanism 54 that cleanses probe arm 46 and sensing device 47.

The present embodiment, therefore, provides retractable electrostatic probe arm 46 with sensing device 47 that cleansing mechanism 54 cleanses upon retraction into housing 36 and isolation by isolation valve 34. The present embodiment cleanses sensing device 47 to ensure that it maintains its original pristine state upon re-entry into fabrication environment 16.

FIG. 2 shows in more detail retractable probe system 12 of the present embodiment. Retractable probe system 12 attaches to flanged portion 60 of process chamber wall 14. Flanged connection isolation valve 34 connects to flanged portion 60 and to flanged portion 62 of housing 36. Gas connection 38 and gas connection 40 attach to housing 36 to permit gas communication within sensing device chamber 64. Cleansing mechanism 54 penetrates housing 36 at BNC connector 66. Cleansing mechanism 54 includes flashing device 68 for biasing sensing device 47.

Within sensing device chamber 64, probe arm 46 attaches to bellows 48. Bellows 48 attaches to flanged portion 72. Flanged portion 72 connects or joins sensor portion 74 to actuator casement 79. Thus, flanged portion 78 of sensor portion 74 attaches to flange 72. Also, threaded end 80 is part of actuator 50 and screws within flange 72. O-rings 82 and 84 maintain an air tight seal between sensor portion 74 and actuator portion 76 of housing 36. However, other sealing mechanisms may be used to maintain the vacuum integrity of process chamber 10.

Actuator 50 includes gas communication ports 42 and 44 that permit flow of a control medium such as a gas or hydraulic fluid to move piston head 77 of actuator rod 52. Actuator casement 79 surrounds actuator 50 and actuator rod 52 to prevent any particulate that may flake or drop from actuator 50 from contaminating the clean room environment of the fabrication reactor.

Actuator rod 52 may be integral to or simply connect to probe arm 46. As such, as piston head 77 moves in response to the flow of the control medium, probe arm 46 will move by the same amount as piston head 77. For example, a control gas may pass through port 44 to enter actuator 50. The control gas passes into actuator 50 to cause piston head 77 to move in the direction of flange 72, which itself is stationary. This moves probe arm 46 in the direction of process chamber wall 14. As piston head 77 moves toward flange 72, control gas also exits port 42. Continued movement of piston head 77 extends probe arm 46 into process chamber 10 and into fabrication environment 16 (see FIG. 1) so that sensing device 47 may sense one or more predetermined process parameters. During this time bellows 48 maintains the vacuum integrity of the process chamber, which as long as isolation valve 34 is open, includes the volume of sensing device chamber 64.

In removing probe arm 46 from fabrication environment 16, control gas passes through port 42 to cause piston head 77 to move away from flange 72. This draws probe arm 46 and sensing device 47 fully into housing 36. Thus, movement of piston head 77 within actuator 50 by a control medium such as a control gas through ports 42 and 44 controls the movement of sensing device 47 in fabrication environment 16. In controlling the location of sensing device 47, a wide variety of techniques have use with the present embodiment. For example, the present embodiment may use microswitches with stops to position piston head 77 at an intermediate point between the ends of actuator 50. On the other hand, simply the full motion of actuator 50 may provide the limiting positions for piston head 77, and, therefore, the limiting positions for sensing device 47. Other locator mechanisms may be part of the present embodiment for precisely controlling the location of sensing device 47 within fabrication environment 16.

Actuator casement 79 is sealed by flange 86 which includes a seal such as O-ring 88. BNC connector 90 penetrates through flange 86 to provide electrical connection to actuator rod 52. To maintain electrical contact with sensing device 47, the present embodiment uses a BNC connector 92, as FIG. 3 illustrates that is soldered to wire 94. Wire 94 passes within actuator rod 52 and makes electrical contact with or may itself operate as sensing device 47. Returning to FIG. 2, bellows 48 attaches to probe arm 46 at flanged connection 96. Flanged connection 96 also includes O-ring 98 or a similar seal to maintain a vacuum-tight or air-tight enclosure between bellows 48 and the internal hollow portion of probe arm 46.

Sensing device 47 is preferably an electrostatic probe capable of determining a wide array of process parameters including, for example, fabrication environment 16 temperature, electronic density within fabrication environment 16, and the potential of plasma gas injection module 26 within fabrication environment 16 to determine the degree of plasma discharge.

OPERATION

Operation of retractable probe system 12 has already been described in significant detail, especially from the viewpoints of mechanical and electrical operation and sensing device 47 cleansing. However, it is appropriate to briefly turn to operation of retractable probe system 12 from the standpoint of in situ cleaning of sensing device 47 during a semiconductor wafer fabrication process. Therefore, returning to FIGS. 1, through 3, a typical fabrication process for wafer 24 may establish a wide variety of fabrication environments 16 within process chamber 10. Examples of such processes, each having a possibly different fabrication environment 16, may be film deposition processes such as chemical vapor deposition (CVD) for forming epitaxial semiconductor layers, dielectric layers of materials such as silicon nitride, silicon oxide or oxinitride, layers of metal such as tungsten or aluminum, or layers of polycrystalline silicon and doped oxides.

In any of these fabrication environments 16, it is important to determine certain process parameters. Thus, as the fabrication environment 16 changes, retractable probe system 12 may direct sensing device 47 into and out of fabrication environment 16 by opening isolation valve 34 and communicating the control medium in actuator 50. As compressed air or gas (e.g., argon, nitrogen or some other inert gas) passes through port 44 of actuator 50, piston head 77 moves toward flange 72. Port 42 is also opened to permit control gas on the flange 72 side of piston head 77 to leave actuator 50. This moves probe arm 46 and sensing device 47 in the direction of process chamber 10 through process chamber wall 14 and into fabrication environment 16.

Once in fabrication environment 16, sensing device 47 may sense the desired process parameter and relay signals resulting from these sensing along connection wire 94 to an associated monitoring system. Withdrawing sensing device 47 from fabrication environment 16 begins by flowing control gas into port 42 and control gas out of port 44. This flow of control gas causes piston head 77 to move in the direction of port 44 until piston head 77 reaches a predetermined point such as complete withdrawal of sensing device 47 into sensing device chamber 64. That is, movement may continue until sensing device 47 fully withdraws in sensing device volume 64 of sensor portion 74 of housing 36 or until probe arm 46 reaches an intermediate point. When sensing device 47 is fully within sensing device chamber 64, isolation valve 34 may be shut to isolate sensing device 47 from fabrication environment 16.

The next step may be to draw a vacuum within sensing device chamber 64 to minimize the amount of process gas from fabrication environment 16 that exists within sensing device chamber 64. A refining gas may then be bled into sensing device chamber 64. This refining gas may be ignited by applying a voltage through BNC connector 66 of cleansing mechanism 54 to energize flashing device 68. Operating flashing device 68 causes the refining gas to ignite into a plasma. This plasma biases and, thereby, cleanses sensing device 47 as well as probe arm 46. This cleansing occurs, however, without contaminating fabrication environment 16 because isolation valve 34 is closed. Then, the spent refining gas may be evacuated from sensing device chamber 64. An aspect of the present embodiment is to also equalize the pressure between sensing device chamber 64 and fabrication environment 16 prior to inserting sensing device 47 back into fabrication environment 16. This prevents disturbing fabrication environment 16 when sensing device 47 is to take another measurement. The present embodiment, therefore, provides for each measurement within fabrication environment 16 a clean sensing device 47, while not contaminating fabrication environment 16 with a refining gas or causing a loss in. process throughout for fabricating semiconductor wafers 24.

The concepts of the present embodiment are directly applicable to all forms of plasma processing including plasma enhanced CVD (PECVD), plasma etch, sputter deposition and processes such as dry deposition. Each of these processes relies on the excitation of atoms or molecules via electron impact or collision. As a result, the invention makes practical in situ monitoring for improving these processes. It may also be practical to include with the present embodiment a feedback and control mechanism to adjust process parameters in response to fabrication environment 16 in situ parameter sensing. These and other changes to the semiconductor device fabrication processes that in situ measurement makes possible are a particularly attractive feature of the present embodiment. That is, the technical advantages that the present embodiment makes possible give the user a significant amount of flexibility that does not exist in heretofore known sensing systems.

A technical advantage of the present embodiment, therefore, is that it is simple to implement for in situ movement of probe arm 46 and sensing device 47 for inserting them into and removing them from semiconductor wafer 24 fabrication environment 16.

Another technical advantage of the present embodiment is that it permits full-scale production of semiconductor wafers without having to open the vacuum of fabrication reactor process chamber 10, remove probe arm 46, scrape off or otherwise clean sensing device 47 and then restore vacuum for further sensing. Avoiding these steps permits continuous formation of semiconductor wafers.

Yet another technical advantage of the present embodiment is that it improves the accuracy of sensing with sensing device 47. By removing the sensing device 47 from fabrication environment 16 and immediately cleaning the sensing device 47 to remove small amounts of deposited material, films do not form on sensing device 47. Consequently, no need exists to scrape the sensing device 47 surface. The present embodiment, therefore, avoids the detrimental effects of changing the sensing surface area as well as changes in sensing accuracy that deposited films and known abrasive cleaning processes can produce. Not only does the method and system of the present invention permit full scale continuous production of semiconductor wafers, but it also improves the accuracy of sensing device 47. By improving the accuracy of the sensing device 47, the present embodiment makes readily possible improvements in the overall quality of the resulting semiconductor wafer.

ALTERNATIVE EMBODIMENTS

There are any number Of alternatives or changes in the design of retractable probe system 12 which may be readily apparent to one of ordinary skill in the art. Such alternatives may not be employed in the device of the preferred embodiment for any number of reasons, such as cost and performance considerations, size constraints, availability of materials, arbitrary design decisions, and the like. A number of these alternatives have been mentioned above. However, it is felt that it may be worthwhile to mention several other alternatives here even further illustrate the broad scope of the present invention. This is, of course, done without limitation of other embodiments which may be equally obvious to one of ordinary skill in the art, but which are not mentioned here because of time and space constraints.

Figure 4:
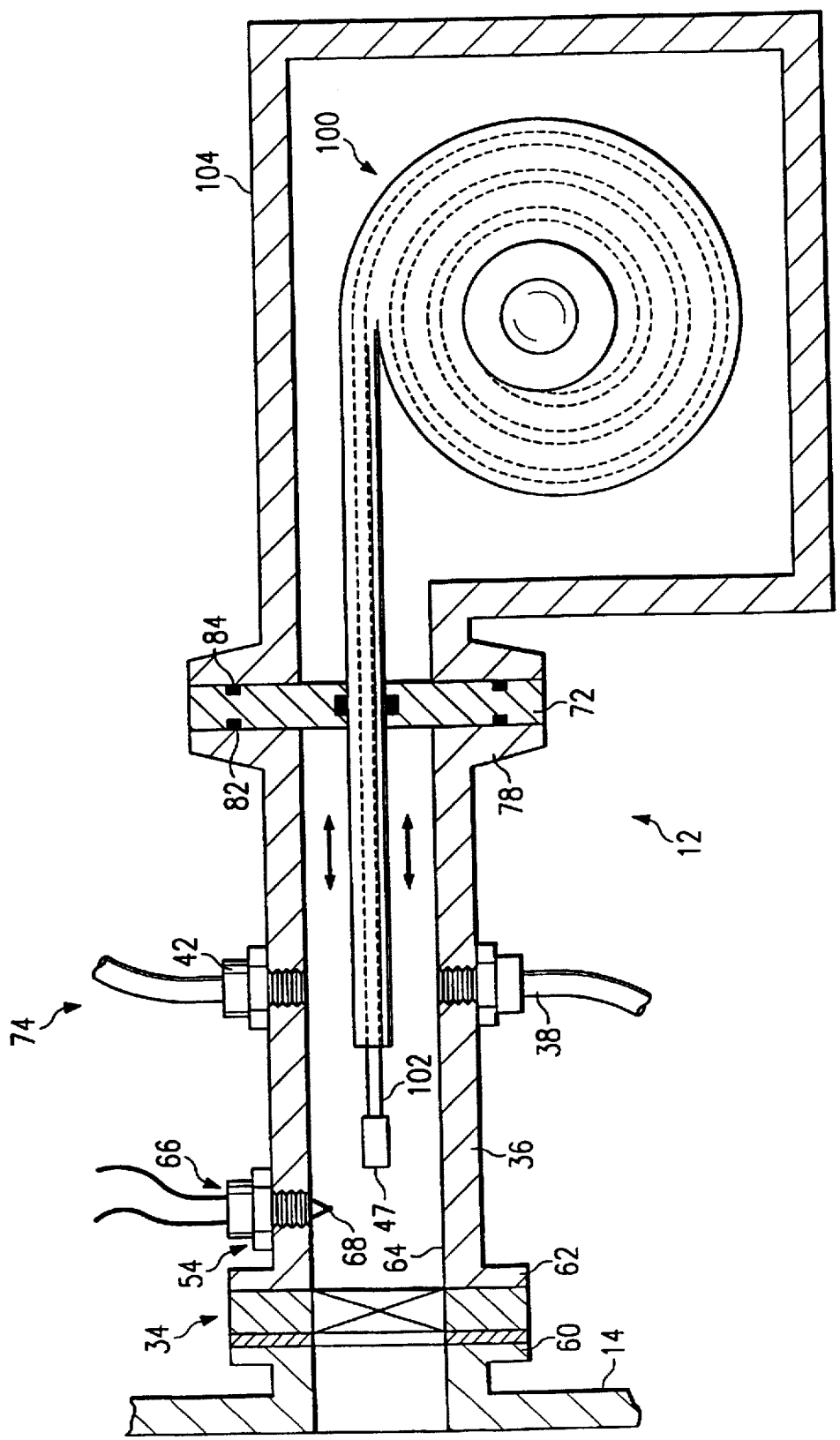
FIG. 4 illustrates an alternative embodiment of the invention.

One alternative embodiment of retractable probe device 10 as appears in FIG. 4 that uses a coil canister 100 instead of actuator 50. By forming a flexible, though sturdy, rod 102 that may be coiled within coiled canister 100, sensing device 47 may be more controllably located within fabrication environment 16. There are, however, other factors, such as cost and maintaining vacuum integrity, that may make use of coiled canister 100 less attractive than using actuator 50. Note that reference numerals appearing in FIG. 4 correspond to the above-identified components in FIGS. 1 through 3. In addition, canister casement 104 surrounds canister 100 much in the same way that actuator casement 79 surrounds actuator 50. Thus, instead of operating actuator mechanism 76 with piston head 77, by simply unwinding and rewinding the coil within coil canister 100, it is possible to introduce sensing device 47 within fabrication environment 16. Cleansing in this alternative embodiment of sensing device 47 may also proceed as described above within sensing device chamber.

There may be other alternatives to the various devices for cleaning sensing device 47. Moreover, there may be more than one sensing device 47. Such configurations are well within the scope of the present invention. Thus, the invention is intended to be limited only by the claims which are meant to cover such obvious alternatives and deviations from the preferred design.

What is claim is:

1. A method for in situ sensing of a semiconductor device fabrication environment process parameter during a fabrication process, comprising the steps of:

sensing a process parameter using a sensing device;

holding the sensing device on a probe arm and extending the sensing device and arm to a first location of the semiconductor device fabrication environment;

receiving the sensing device and probe arm in a housing;

controllably locating the sensing device and the probe arm within the fabrication environment and within the housing;

isolating the sensing device and the probe arm within the housing and essentially out of gaseous communication with the fabrication environment; and cleaning the sensing device within the housing and immediately thereafter locating the sensing device in the fabrication environment.

2. The method of claim 1, wherein said cleaning step further comprises the step of cleaning the sensing device when the sensing device is out of gaseous communication with the fabrication environment.

3. The method of claim 1, wherein the sensing step comprises the step of sensing the electron temperature within the fabrication environment during plasma processing.

4. The method of claim 1, wherein said locating step comprises the step of extending an actuator mechanism comprising a piston head in response to a control medium flowing through said actuator mechanism for moving the probe arm and the sensing device in the fabrication environment.

5. The method of claim 1, wherein said sensing step further comprises the step of measuring the electron density of the fabrication environment in situ.

6. The method of claim 1, further comprising the step of evacuating the housing to remove fabrication environment gases and free radicals within the housing.

7. The method of claim 1, wherein said cleansing step further comprises the step of directing within the housing a refining gas and forming from the refining gas a an active cleansing environment for removing fabrication environment gases and free radicals from the sensing device.

8. The method of claim 1, further comprising the step of equalizing the pressure between the fabrication environment and the housing prior to inserting the sensing device and the probe arm into the fabrication environment.

9. The method of claim 1, further comprising the steps of automatically controlling and performing of said locator step, said isolating step, and said cleansing step using a process control computer.

10. The method of claim 1, wherein said probe arm comprises a flexible and further comprising the step of holding the sensing device in a horizontal plane on the probe arm and forming a coil and further wherein said isolating step comprises operating a coil device to coil and uncoil the probe arm and so as to insert and remove the probe arm and sensing device from the fabrication environment in situ a wafer fabrication process.

* * * * *